United States Patent [19]

Ekholmer

[11] Patent Number: 4,717,379
[45] Date of Patent: Jan. 5, 1988

[54] CATHETER, PROBE OR SIMILAR DEVICE

[75] Inventor: Erik Ekholmer, Danderyd, Sweden

[73] Assignee: Mediplast AB, Solna, Sweden

[21] Appl. No.: 841,516

[22] PCT Filed: Jul. 1, 1985

[86] PCT No.: PCT/SE85/00267
§ 371 Date: Feb. 28, 1986
§ 102(e) Date: Feb. 28, 1986

[87] PCT Pub. No.: WO86/00232
PCT Pub. Date: Jan. 16, 1986

[30] Foreign Application Priority Data

Jun. 29, 1984 [SE] Sweden ............................. 8403474

[51] Int. Cl.$^4$ ............................................. A61M 25/00
[52] U.S. Cl. .......................................... 604/43; 604/280
[58] Field of Search ................................. 604/43–45, 604/265, 266, 280, 282

[56] References Cited

U.S. PATENT DOCUMENTS

| | | | |
|---|---|---|---|
| 2,470,665 | 5/1949 | Stiehl | 604/96 |
| 2,548,602 | 4/1951 | Greenburg | 128/344 |
| 2,614,563 | 10/1952 | Devine | 604/45 |
| 2,930,378 | 3/1960 | Buyers | 604/45 |
| 3,598,127 | 8/1971 | Wepsk | 604/265 |
| 3,981,299 | 9/1976 | Murray | 604/43 |
| 4,186,745 | 2/1980 | Lewis et al. | 604/265 |
| 4,406,656 | 9/1983 | Hattler et al. | 604/280 |

FOREIGN PATENT DOCUMENTS

WO85/00526  2/1985  PCT Int'l Appl. ................. 604/266

Primary Examiner—Dalton L. Truluck
Attorney, Agent, or Firm—Cushman, Darby & Cushman

[57] ABSTRACT

A catheter, probe or a similar device is intended to be inserted into a body cavity. The catheter (1) is double-walled over a substantial portion of its length, at which the inner wall (5) on the outside and/or the outer wall (6) on the inside is provided with longitudinal partitions for forming separate longitudinal passages (3) between the walls (5,6). The passages (3) are perforated from the outside of the catheter by a plurality of capillary holes (4). Into at least some of the passages (3) a fluid, i.e. compressed air or liquid, or a cream or gel-like substance, is intended to be inserted for obtaining a lubrication of the mucous membranes of the body cavity during the insertion. Thus, irritation of the mucous membranes of the body cavity is avoided during the insertion and longer insertion periods are permitted without risk of infection.

6 Claims, 4 Drawing Figures

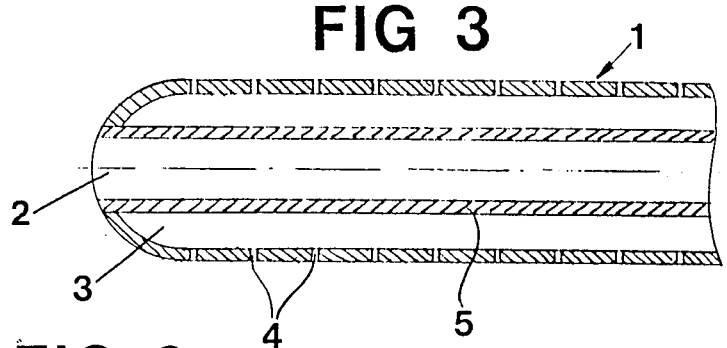
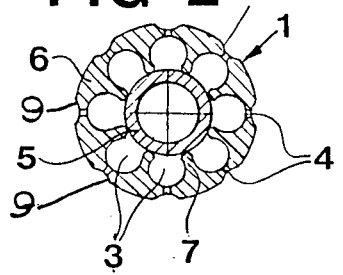
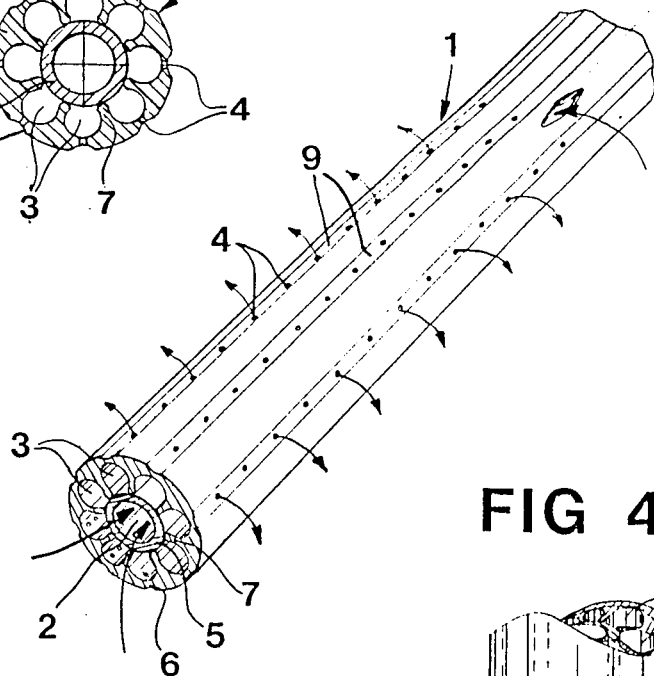
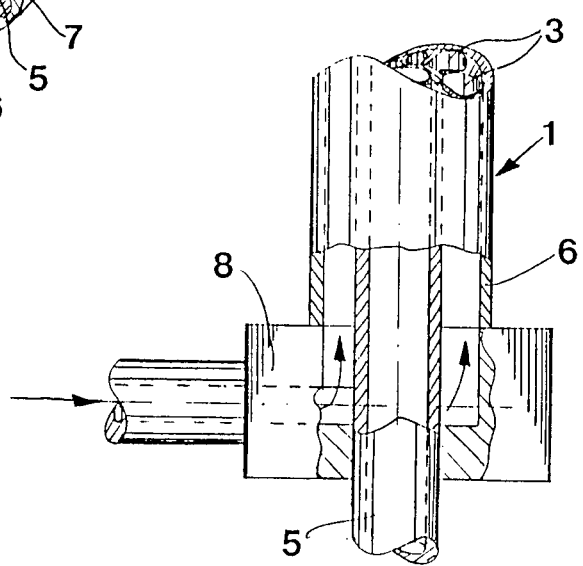

CATHETER, PROBE OR SIMILAR DEVICE

BACKGROUND OF THE INVENTION

1. Field of the Invention

The present invention relates to a catheter, probe or similar device intended to be inserted into a body cavity and which over a substantial portion of its length is double-walled, at which the outer wall through a plurality of capillary holes communicates with the outside of the catheter.

2. Description of the Related Art

A problem which occurs during the insertion of a catheter, probe and the like is dessication and irritation of the mucous membranes on the inside of the body cavity, which can lead to infections.

In U.S. Pat. No. 3,981,299 there is shown an urethral catheter which over a portion of its length is covered by a thin flexible membrane having a plurality of holes. In the space between the membrane and the catheter, a liquid or other substance can be injected. All the holes communicate with each other.

SUMMARY OF THE INVENTION

The object of the present invention is to provide a catheter, probe or the like which is easy to insert without irritating the mucous membranes and which also permits longer insertion periods without any risk of infection. It is desirable that all capillary holes do not communicate with each other but that some holes can be used for supplying a washing agent, while other holes are used for draining the washing agent and any possible secretion from the body cavity. Besides, the catheter should be simple to manufacture. According to the invention this simplicity has been achieved by the fact that the inner wall on the outer tube and the outer wall on the inner tube is provided with longitudinal partitions for making separate longitudinal passages between the walls. These passages are in communication with the capillary holes.

The invention will be described below in details with reference to a pair of embodiments shown in the enclosed drawings.

FIG. 1 shows in a broken perspective a catheter according to the invention.

FIG. 2 is a transverse section through the catheter according to FIG. 1.

FIG. 3 is a longitudinal section through the insertion end of the catheter according to a somewhat modified design.

FIG. 4 shows a partly broken section through the rear end of the catheter.

DESCRIPTION OF THE PREFERRED EMBODIMENTS

The catheter 1 shown in FIG. 1 has a central flow channel 2 and a plurality of axial passages 3 arranged radially outside said channel 2 and regularly arranged along the circumference thereof. The passages 3 are perforated with a large number of very small capillary holes 4 from the outside of the catheter 1. These holes 4 can be located in longitudinal cavities or recesses 9 on the outside of the catheter 1 as is shown in FIGS. 1 and 2 or have a chamferred edge outwards (FIG. 3) in order to avoid damage to the mucous membranes.

To the axial passages 3 there is intended to be connected e.g. a compressed air source or a fluid pressure, so that a lubrication of the outside of the catheter 1 can be obtained during the insertion thereof. It is also possible that during the insertion time a continuous or intermittent washing of the catheter 1 can be performed in order to reduce the irritation of the mucous membrane and eliminate the risk of infection. It is also possible to alternately connect the passages 3 to a pressure or suction source so that some of the passages 3, i.e. every other one, is connected to a pressure source while the other passages 3 are connected to a suction source. In this way a draining of the washing agent and any possible secretion from the body cavity can be obtained.

Another possible manner in which to utilize the capillaries 4 is to fill the axial passages 3 with a gel- or cream like agent, which is wiped against the walls of the body cavity at the contact therewith in order to lubricate the outside of the catheter 1. The capillaries 4 are by capillary action filled with more agent as long as a sufficient amount of agent is present in the axial passages 3. This action implies that the passages 3 are closed at the introduction end of the catheter 1, as is shown in FIG. 3.

The manufacturing of the catheter 1 can be done in different ways, one of them is coextrusion of two tubes, an inner circular tube 5 and an outer tube 6, which on the inside has longitudinal partitions 7 for making the axial passages 3. Of course it would be possible to instead provide the inner tube 3 with longitudinal partitions 7 on the outside, at which the outer tube 6 can be plane.

By making the outer tube 6 somewhat shorter than the inner tube 3 it is possible to connect a connection member 8 (FIG. 4) for supplying compressed air, liquid or cream to the axial passages 3. The catheter 1 can of course also be manufactured in only one piece.

The invention is not limited to the illustrated and described embodiments but a plurality of variants are possible within the scope of the claims.

I claim:

1. A catheter having two ends and being adapted to be inserted at one end into a body cavity, said catheter comprising:
   an inner tube and an outer coaxial tube, both of said tubes having exterior and interior surfaces;
   longitudinal partitions extending between the exterior surface of the inner tube and the interior surface of the outer tube;
   said longitudinal partitions defining separate longitudinal passages between the exterior surface of the inner tube and the interior surface of the outer tube;
   said outer surface of the outer tube having a plurality of capillary holes extending therethrough and communicating with the longitudinal passages; and at least some of the longitudinal passages being adapted to be attached to a pressure source means for supplying fluid which is admitted to penetrate the plurality of capillary holes into the body cavity outside of the catheter.

2. The catheter according to claim 1 wherein:
   other longitudinal passages are adapted to be connected to a suction source means for draining fluid from the body cavity outside of the catheter through the plurality of capillary holes in communication therewith.

3. The catheter according to claim 1 wherein:
   said outer surface of the outer tube has chamfered edges around the plurality of capillary holes.

4. The catheter according to claim 1 wherein:

said outer surface of the outer tube has recessed cavities around the plurality of capillary holes.
5. The catheter according to claim 1 wherein:
said outer tube is shorter than said inner tube at the other end of the two ends of the catheter.

6. The catheter according to claim 5, further comprising:
means, attached to at least some of the longitudinal passages, for connecting the pressure source means to the shorter outer tube around the inner tube.

* * * * *